United States Patent
Feng et al.

(10) Patent No.: US 9,205,277 B2
(45) Date of Patent: Dec. 8, 2015

(54) COLOR ADAPTIVE THERAPEUTIC LIGHT CONTROL SYSTEM

(75) Inventors: Xiao-Fan Feng, Camas, WA (US); Hiromi Katoh, Nara (JP)

(73) Assignee: Sharp Laboratories of America, Inc., Camas, WA (US)

( * ) Notice: Subject to any disclaimer, the term of this patent is extended or adjusted under 35 U.S.C. 154(b) by 0 days.

(21) Appl. No.: 13/401,183

(22) Filed: Feb. 21, 2012

(65) Prior Publication Data

US 2013/0218240 A1 Aug. 22, 2013

(51) Int. Cl.
*A61N 5/06* (2006.01)
*A61M 21/00* (2006.01)

(52) U.S. Cl.
CPC .............. *A61N 5/0618* (2013.01); *A61M 21/00* (2013.01); *A61M 2021/0044* (2013.01); *A61M 2205/3306* (2013.01); *A61M 2230/06* (2013.01); *A61M 2230/42* (2013.01); *A61M 2230/50* (2013.01); *A61M 2230/63* (2013.01); *A61N 2005/0663* (2013.01)

(58) Field of Classification Search
CPC ........... A61N 5/0616; A61N 2005/063; A61N 2005/0652; A61N 2005/0645; A61N 2005/0642; A61N 2005/0663; A61N 5/0618; A61N 2005/0651; A61N 5/0621; A61N 2005/0644; A61N 2005/066; A61N 5/0617; A61N 2005/0602
USPC ...................................................... 607/88–94
See application file for complete search history.

(56) References Cited

U.S. PATENT DOCUMENTS

| | | | |
|---|---|---|---|
| 6,350,275 B1 | 2/2002 | Vreman et al. | |
| 6,554,439 B1 | 4/2003 | Teicher et al. | |
| 6,866,678 B2 * | 3/2005 | Shenderova et al. | ............ 607/88 |
| 6,955,684 B2 | 10/2005 | Savage, Jr. et al. | |
| 7,679,281 B2 | 3/2010 | Kim et al. | |
| 7,845,822 B2 | 12/2010 | Bierhuizen et al. | |
| 2007/0268234 A1 | 11/2007 | Wakabayashi et al. | |
| 2008/0219013 A1 | 9/2008 | Budinger et al. | |
| 2008/0275533 A1 | 11/2008 | Powell | |
| 2009/0240311 A1 | 9/2009 | Andersen | |
| 2009/0326616 A1 | 12/2009 | Aarts et al. | |
| 2010/0171441 A1 | 7/2010 | Schlangen et al. | |
| 2010/0174345 A1 | 7/2010 | Ashdown | |
| 2010/0244735 A1 | 9/2010 | Buelow, II | |

OTHER PUBLICATIONS

Mark S. Rea et al., The potential of outdoor lighting for stimulating the human circadian system, Alliance for Solid-State Illumination Systems and Technologies (ASSIST) Report, May 13, 2010, 11 pgs.
M. G. Figueiro et al., "Developing Architectural Lighting Designs to Improve the Health and Well-being of Older Adults," AIA report on University Research, vol. 3, 2005, 26 pgs.

(Continued)

*Primary Examiner* — William Thomson
*Assistant Examiner* — Jeffrey Lipitz
(74) *Attorney, Agent, or Firm* — Chernoff Vilhauer McClung & Stenzel, LLP

(57) ABSTRACT

A system for influencing a state of a user includes a light source for emitting light influencing the state of the user. The system includes a light controller selectively controlling the emission of the light and an analysis engine which provides a signal to the light controller indicating a desired emission of the light. The system selectively directs blue light from the light source onto a material that retransmits it as a light different than blue light.

20 Claims, 16 Drawing Sheets

(56) References Cited

OTHER PUBLICATIONS

Mark S. Rea et al., "Circadian light," Journal of Circadian Rhythms, Feb. 2010, 10 pgs.

Oliver Stefani, "Evaluation of Human Reactions on Displays with LED Backlight and a Technical Concept of a Circadian Effective Display," SID 2010 Symposium digest, 2010, pp. 1120-1123.
Sharp Corporation Press Release, http://sharp-world.com/corporate/news/100819.html., Aug. 19, 2010, 5 pgs.

* cited by examiner

FIG. 1 LED CEILING LIGHTS

COLOR ADAPTIVE THERAPEUTIC LIGHT CONTROL SYSTEM

CROSS-REFERENCE TO RELATED APPLICATIONS

Not applicable.

BACKGROUND OF THE INVENTION

The present invention relates generally to a therapeutic light control system.

The biological circadian rhythm in humans control important processes, such as the daily cycle of waking and sleeping. This biological rhythm tends to align its cycle to the external environment, such as the exposure of light modifying the hormone melatonin levels, which are associated with sleep. A relatively low melatonin level stimulates alertness while a relatively high melatonin level increases sleepiness. The melatonin synthesis is reduced when light impacts the retina of the eye. It may be desirable to modify the circadian rhythm to increase the well being of the person.

Aarts et al., U.S. Patent Application Publication 2009/0326616 disclose a system that influences a photobiological state of a person. The system includes a light source, a sensor that senses a first biophysical parameter of a person that is sent to a control circuit which sends a control signal to the light source so as to generate a predetermined photobiological state. The control signal provided by the control circuit is based upon the first biophysical parameter and another parameter, such as a biophysical parameter sensed at a different time.

Referring to FIG. 1, an exemplary LED based ceiling light allows the use of a remote controller to change the color of a white light with an adjustable color function and to adjust the brightness with the dimmer function. These functions combine to offer 110 different levels of color and brightness that match the mood or time of day. These lights also feature an eco-light rhythm function, a lighting program that automatically adjusts the color and brightness throughout the day. For example, the light may match the lifestyle rhythm of the user by giving crisp, cool daylight white for a refreshing wake-up in the morning, or a warm white in the evening when a relaxing atmosphere is desired.

The foregoing and other objectives, features, and advantages of the invention will be more readily understood upon consideration of the following detailed description of the invention, taken in conjunction with the accompanying drawings.

DETAILED DESCRIPTION OF PREFERRED EMBODIMENT

While a light system provides wellness benefits to a user, different users tend to have different responses to the application of light. With different users having different responses to the application of light, it is desirable to include a feedback to the system so that the system may be suitably tuned to the particular user's characteristics. While many users will tend to have similar characteristics, most users will have somewhat different responses to the application of light for therapeutic and wellness benefits. With a suitable application of light, selected for the particular user based upon their individual characteristics, the user may achieve the improved health and wellness benefits.

By way of example, suitable exposure to light may provide responses that are shorter term (such as 0-3 hours of exposure) which are generally psychological in nature. For example, the application of an appropriate amount of soothing lights in a proper manner may calm the user and reduce their heart rate. By way of example, suitable exposure to light may provide responses that are longer term (such as several hours to days) which is primarily circadian in nature as controlled by melatonin levels.

Figure 1:
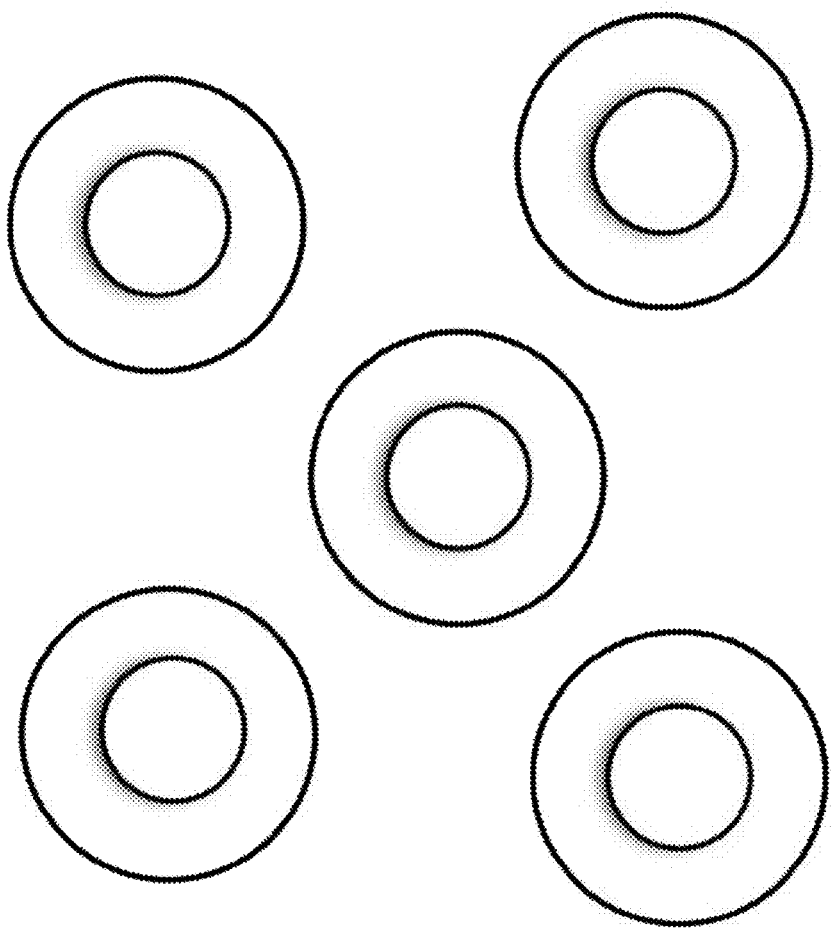
FIG. 1 illustrates a light source.
Figure 2:
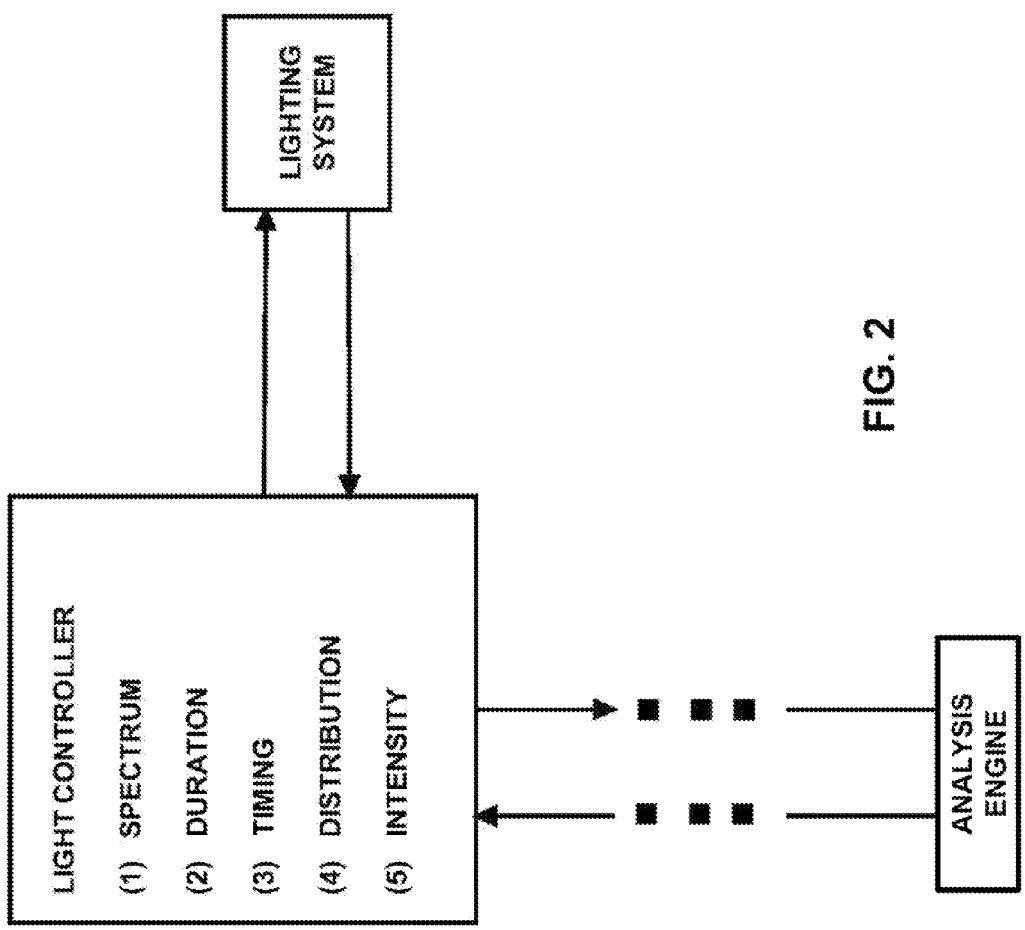
FIG. 2 illustrates a light controller and lighting system.

Referring to FIG. 2, a lighting system may be controlled by a light controller to manage a number of different attributes, each of which may individually or collectively contribute to the wellness and health of a user. The lighting system may include any suitable type of light source, such as for example, a luminaire, ceiling lights, a floor lamp, a desk lap, head worn goggles, a backlit display, or a combination thereof. The lighting system is preferably capable of generating light in the spectrum range of 420 nm to 500 nm for circadian system stimulation, although any spectrum may be used. A first aspect of the lighting system may be the color spectrum of the lights. For example, the lighting system may have multi-colored lights which may be selected to provide desired color or colors to the user. For example, the lighting system may provide a selected color spectrum to the user among a set of different selectable color spectrums including different color temperatures, i.e., warm or cold light. For example, the color spectrum may be modulated or otherwise temporally varied. For example, the relative intensity of the output of a multi-colored light emitting diode set may be varied. A second aspect of the lighting system may be the duration of illumination of the lights. For example, the lighting system may provide illumination for one or more selectable durations to the user. A third aspect of the light system may be spatial distributions or positions of one or more of the lights. For example, the lighting system may have a one dimensional light arrangement, a two dimensional light arrangement, or a three dimensional light arrangement where selected lights are illuminated. For example, the lighting system may have a plurality of light sources (or otherwise the distribution of illumination from a light source) that may be spatially and/or temporally selectable. A fourth aspect of the light system may be the brightness of the lights. For example, the lighting system may selectively provide a low illumination to the user, a medium illumination to the user, and/or a high illumination to the user in a manner to contribute to the wellness and the health of the user. For example, the lighting system may selectively have different brightness for different light sources illuminating the user. A fifth aspect of the light system may be the timing of the light or lights. For example, one or more selected lights may be turned on during different parts of the day in different manners.

By selectively modifying one or more of these five different lighting attributes, or other attributes, various wellness and health attributes for the user may be modified. In particular, these modifications should be based upon the particular user so that the most effective wellness and heath benefits may be achieved. By way of example, suitable modification of one or more of these lighting attributes may manage sleep disorders, child hyperactivity learning disorders, elderly safety (e.g., fall avoidance), mental state, and concentration. The biological rhythms may be generally reset by an exposure to an external stimulus with the melatonin suppression peaks at generally blue light having a wavelength around generally 450 nm.

Figure 3:
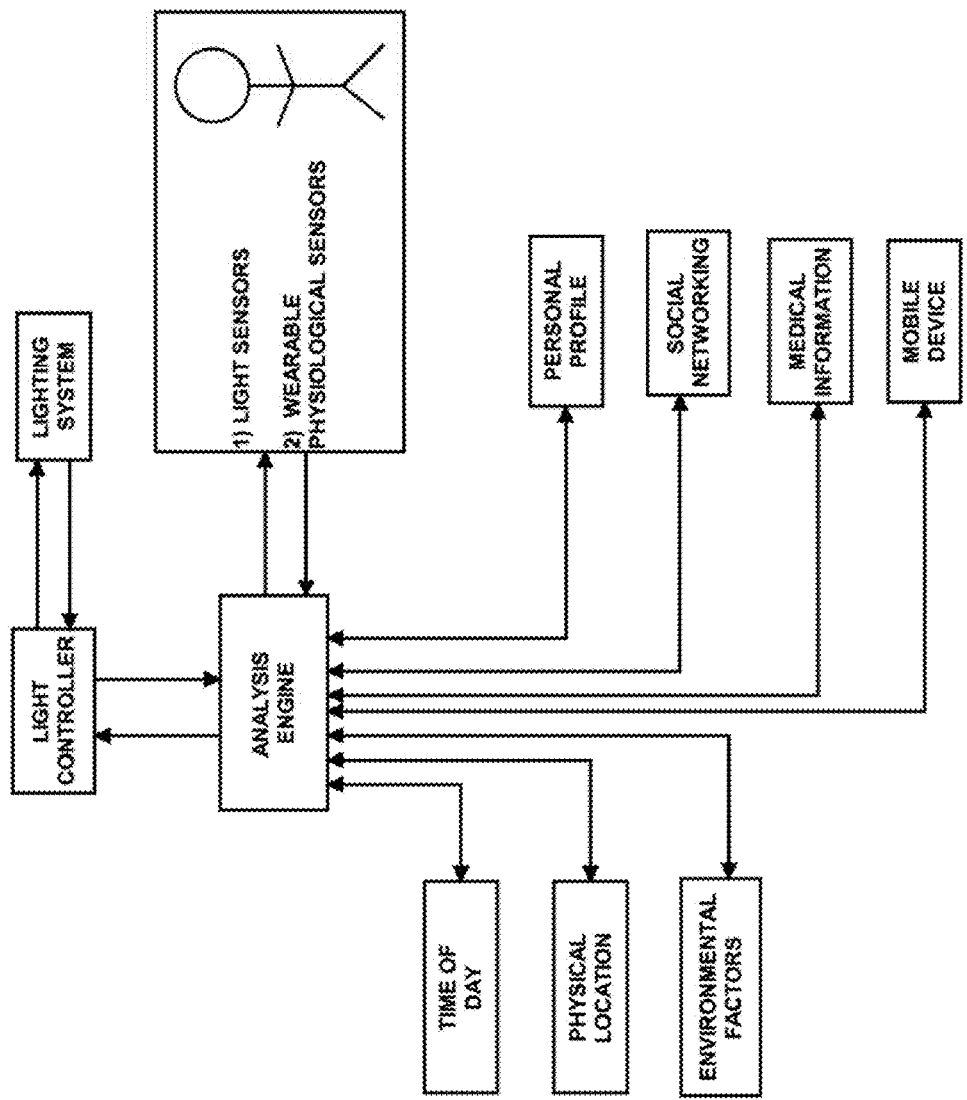
FIG. 3 illustrates a light control system.

Referring to FIG. 3, an analysis engine may be used to selectively control the light controller interconnected to the lighting system. The analysis engine may be operating on a local computer, a service on the Internet, or operating on a cloud computing platform, or otherwise. In some cases, a service provider may be provided to the user to which they may subscribe that provides suitable health services, customizable to the user. The service may be a subscription service to which the user subscribes. The light controller and analysis engine may be separate, or included as separate (or the same) processes on the same device. Also, the different components of the system may be interconnected using any suitable technique, such as wired or wireless communication. The analysis engine may receive input regarding the time of day. The time of day information may be any suitable time based information, such as for example, (1) the current time of the day; (2) morning, afternoon, evening, or night; (3) a weekday or a weekend; (4) a holiday; (5) a particular day of the week; and/or (6) a season of the year. For example, the user may have different requirements in the evening versus the morning. For example, the user may have different requirements during the work week rather than the weekend. For example, a holiday may be a stressful time for the user and thus have different requirements than a non-holiday. For example, a user may have different requirements during the winter than the summer.

The analysis engine may also receive input regarding the user's general physical location. For example, a user in Alaska may have different requirements than a user in Colorado, which may likewise be different than the requirements for a user in Hawaii. In addition, the combination of the user's location together with the time of year may have result in different requirements. For example, a user in Alaska during the winter may have different requirements than either a user in Hawaii during the winter or a user in Alaska during the summer. For example, a user being in their home or at the office may result in different requirements.

The analysis engine may also receive environmental factors regarding the user's current environment. Such environmental factors may include, for example, the current weather forecast; whether it is raining; whether it is foggy; whether it is sunny; whether it is overcast; whether it is hailing; whether it is lightening; whether it is flooding; whether it is cloudy; the current temperature; the anticipated temperature; the barometric pressure; and trends with all of the above. The environmental factors may likewise include current social conditions.

The analysis engine may also receive a personal profile of the user. The personal profile may include information particularized to the user. Some of this particular information may include, for example, whether the user is a morning person or an evening person. The information may include an ophthalmologic characterization of the user, which is especially useful when the lighting system administers light using goggles worn close to the user's eyes. The profile may be specific to a particular user, a particular family, a group of people, or otherwise one or more users. The analysis engine may likewise base its processing on more than one profile, such as an average of a pair of profiles. In addition, the profile or profiles to be used by the analysis engine may be selected by a user or automatically selected by the system or otherwise selected based upon other input. Also, the profile may include health information for the user.

In many cases, users do not have the desire or motivation to manually create a profile. In this case, the user may link their profile to a social network account, such as for example, a Facebook account, a Twitter account, or a MySpace account. The analysis engine retrieves personal information from the social networking account, such as, relationship status, birthday, hometown name, hometown location, sex, employer, college, high school, interests, mood, political views, religious views, activities, interests, music, books, movies, television, and/or occupation. In addition, the user may enter information about their current and/or previous status into the social networking service that may be indicative of their state of mind or otherwise. Since a user tends to have friends, acquaintances, or others linked to their social networking account that are similar to themselves, similar information from another's account may be likewise used by the analysis engine. In addition, the personal profile may include a medical profile of the user, or otherwise the personal profile may be linked to an account that includes medical information, preferably medical information that is otherwise periodically updated. Moreover, some of the information in the user profile may be provided by answers to a set of questions. Personal profile may contain information about the mental state of the individual where such state is determined by the answers that the individual provides to a set of questions indicative of individual's focus and alertness. These may include gender, age, activity and/or other profile information The data obtained or otherwise determined as a result of the therapy, together with the results of the therapy, may be provided to the user's medical provider so that they can monitor the therapy. In general, the analysis engine may receive information from a variety of different sources, and may likewise provide information to the sources, as desired.

In some cases, the user's profile may be periodically synchronized from the user's mobile device. By using wireless, Bluetooth, or other communication techniques, the user's mobile device may provide personal information to the analysis engine about the user.

In addition, sensors associated with the user may likewise provide data to the analysis engine. The sensors may include physiological sensors and light sensitive sensors in the environment of the user. Preferably, the light sensitive sensors and the physiological sensors are worn by the user. The physiological sensors may include, for example, heart rate sensors, time sensors, date sensors, location base sensor, acoustic sensor, body temperature sensor, respiration rate sensor, and/or motion sensor. The physiological sensor information accordingly provides information regarding the user's body. For example, if the user's heart rate is elevated then the analysis engine may be used to provide a light signal to reduce the heart rate. Likewise, the analysis engine may use the other information to provide health benefits. The light sensitive sensors, may be for example, a daysimeter device or a camera type sensor.

In some situations, the level or amount of exposure of light to a user in general, or a particular user, may be higher than a suitable level. In many cases, excessive exposure to light may in fact decrease the user's heath. In other cases, a sensor may sense the light exposure level to an individual's retina, and thus check and confirm that safety standards prevent toxicity by controlling light dosage. Accordingly, the analysis engine may use the light sensing information to determine safe lighting levels.

The system may further operate in a close-loop configuration, if desired. The analysis engine while receiving information from many sources, can likewise provide control or feedback signals to lighting controller, and control or feedback signals to the physiological or light sensors and sources of data. For example, the analysis engine could provide feedback for the configuration of the sensors so that they acquire data in a more suitable manner or other configuration data. For example, the analysis engine could provide feedback for goggles worn by the user to control the amount of light received by the user. For example, the analysis engine may update the personal profile with other information. The analysis engine may likewise receive feedback from the light controller and light sensors so that it may monitor the light that is actually provided to the user. For example, the analysis engine may chose to invoke selected sensors to probe specific different characteristics, such as certain sensors placed at certain positions/locations in the house. In this manner, not all of the sensors need to be on at all times or otherwise configured in a particular. Also, the analysis engine also adjusts the sensitivity of individual sensors that are used to collect the data as needed to suitably control the lighting system.

One location that a user spends considerable time is driving a vehicle or a passenger in a vehicle, especially when driving long distances in the vehicle. Within a typical vehicle many different components include light sources, such as overhead lights, instrument panel lights, navigation system lights, and stereo lights. Also, the vehicle may include additional light sources, if desired. The vehicle may likewise include sensors that are provided within the vehicle, such as sensors in the seat, seatbelt, steering wheel, door, floor, pedals, on the driver's body, or otherwise. The analysis engine may use information from these sensors to adjust the lighting that is available in the vehicle though the windows in a manner to improve the health or alertness of the driver. In addition, the analysis engine may modify the sensors or otherwise select sensors. Also, the analysis engine may selectively reduce the external light or increase the external light by modifying the transmission of light into the vehicle. This modification of external light may be achieved, for example, by changing the tint on the windows by an electrical signal, or otherwise raising and lowering a shade over the windows. In many cases, the user enters in a destination into a navigation system that may be used as the basis to provide characteristics of the anticipated drive. Such characteristics may include the travel time, the traffic conditions, the average speed, the acceleration of the vehicle, and other information. The analysis engine may further use this navigation information to modify the lighting to the user in a manner to improve their health or alertness level.

In many cases it is desirable to increase or otherwise decrease the amount of light from the light provided by the light source to modify the melatonin levels, such as to increase or suppress the melatonin levels. In other cases, it is desirable to modify the spectral peaks or the spectral distribution from the light provided by the light source to modify the melatonin levels. In general, the blue spectrum has the greatest effect on the melatonin levels of the viewer, so it is desirable to modify the blue spectrum of the light source.

Figure 4:
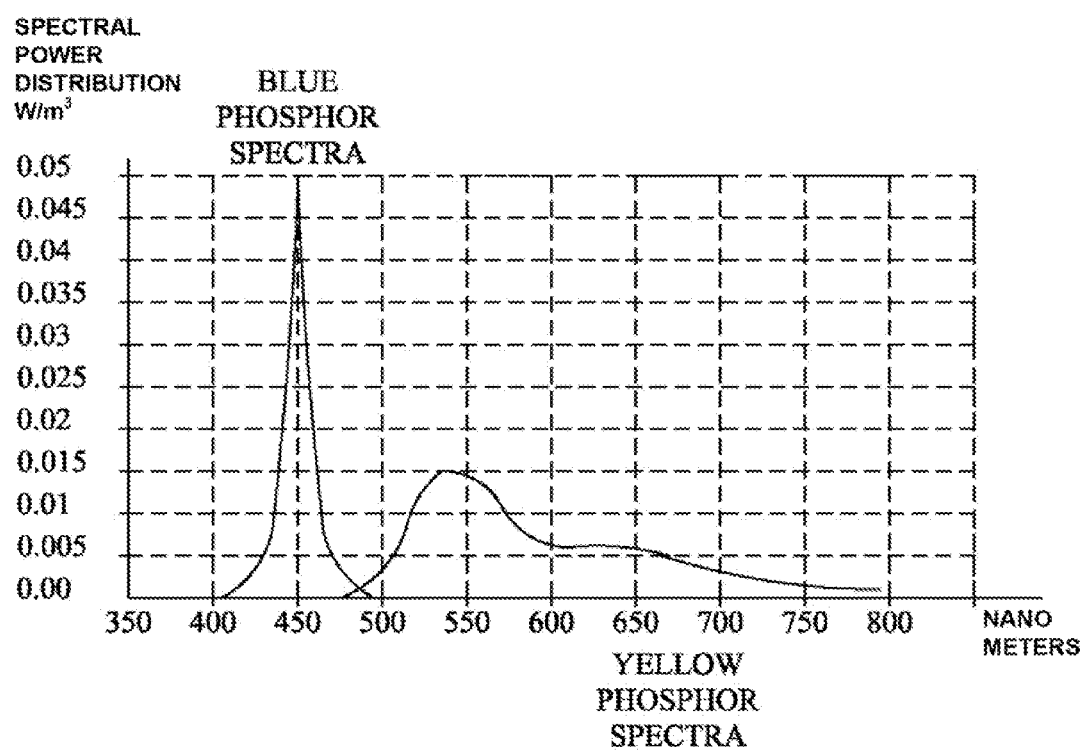
FIG. 4 illustrates a spectral response of a light emitting diode.

Referring to FIG. 4, the spectrum of a white light emitting diode typically includes a blue primary peak spectra generally around 450 nm and a broad secondary peak spectra as a result of a Stokes shift to a longer wavelength as a result of a yellow phosphor within the diode. The 450 nm spectrum is near the peak of the human melatonin suppression wavelength. The substantially higher wavelengths of the spectrum typically have minor impact, if any, on the melatonin suppression. The light emitting diode preferably may switch between the two peaks (or otherwise modify its output) to achieve the desired circadian modulation. For example, in the morning a stronger blue peak together with a weaker yellow peak may be provided, while in the evening a weaker blue peak may be provided together with a stronger yellow peak.

Figure 5:
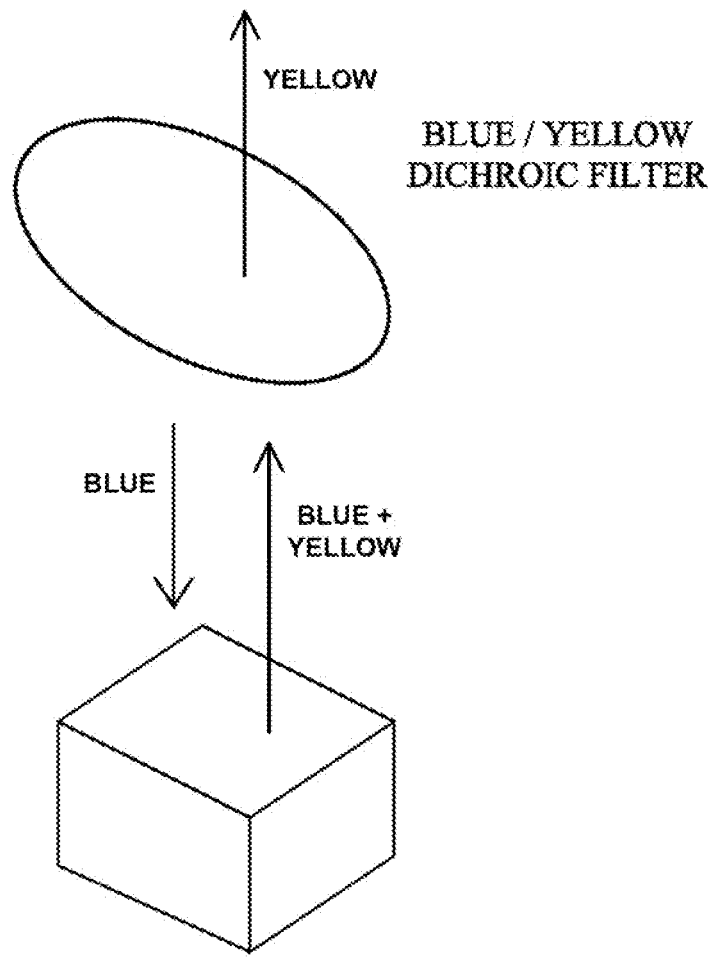
FIG. 5 illustrates a filtering technique for converting blue light to yellow.

Referring to FIG. 5, one technique to selectively increase the blue spectrum of the light emitting diode is to selectively include a blue/yellow dichroic filter in the path of the light from the light emitting diode. The dichroic filter tends to substantially transmit yellow light while substantially reflecting blue light. At least a part of the light, such as the blue light, is reflected back to the light emitting diode, which is then converted by a Stokes shift to a longer wavelength as a result of the yellow phosphor within the diode. Thus, the result of selectively using the additional dichroic filter is to decrease the amount of blue light output from the device, thus the system may selectively increase and decrease the amount of the blue output spectrum. In addition, selectively using the additional dichroic filter increases or decreases the amount of light output from other regions of the visible spectrum. In many cases, the dichroic filter and the yellow phosphor may be integrated on the same substrate with the phosphor layer on the light emitting diode side of the structure.

The amount of the conversion may be controlled by the amount of coverage the filter has over the light emitting areas. If all the LEDs are covered with the dichroic filter, then there will be comparatively little blue light from the LED. If all the LEDs are not covered with the dichroic filter, then there will be comparatively more blue light from the LED. Also, if the dichroic filter is only in part of the optical path then the amount of blue light from the LEDs will be in between. The dichroic filter may be selectively moved into and out of the optical path from the light emitting diodes. Other techniques may likewise be used to selectively include more or less of the dichroic filter in the optical path. The filter coverage may be implemented using any suitable technique, such as a manual slider in and out of the optical path, an automatic switch with an electro-magnetic mechanism, and/or multiple electro-magnetic switches. Similarly, other filtering techniques may likewise be used to selectively reflect light back to the light emitting diode.

Figure 6:
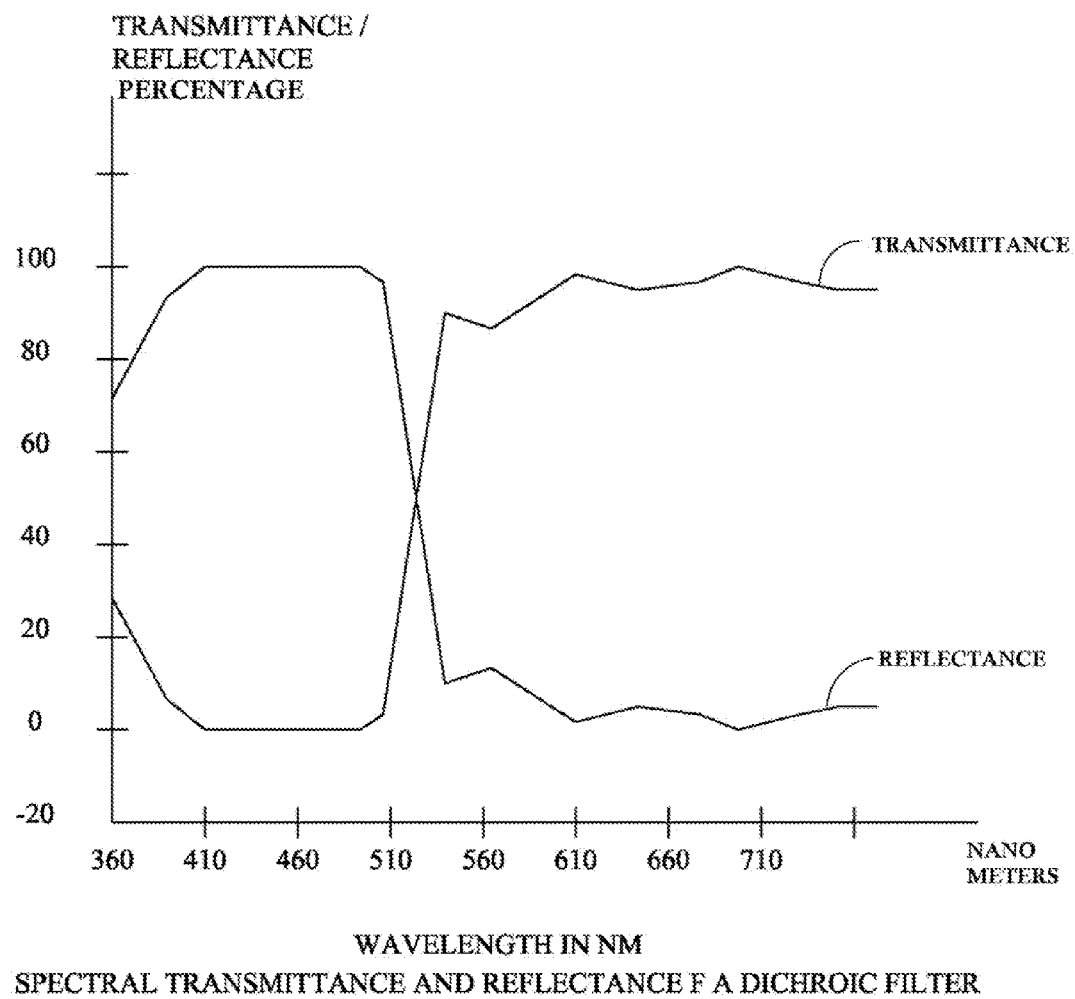
FIG. 6 illustrates spectral transmittance and reflectance of a dichroic filter.
Figure 7:
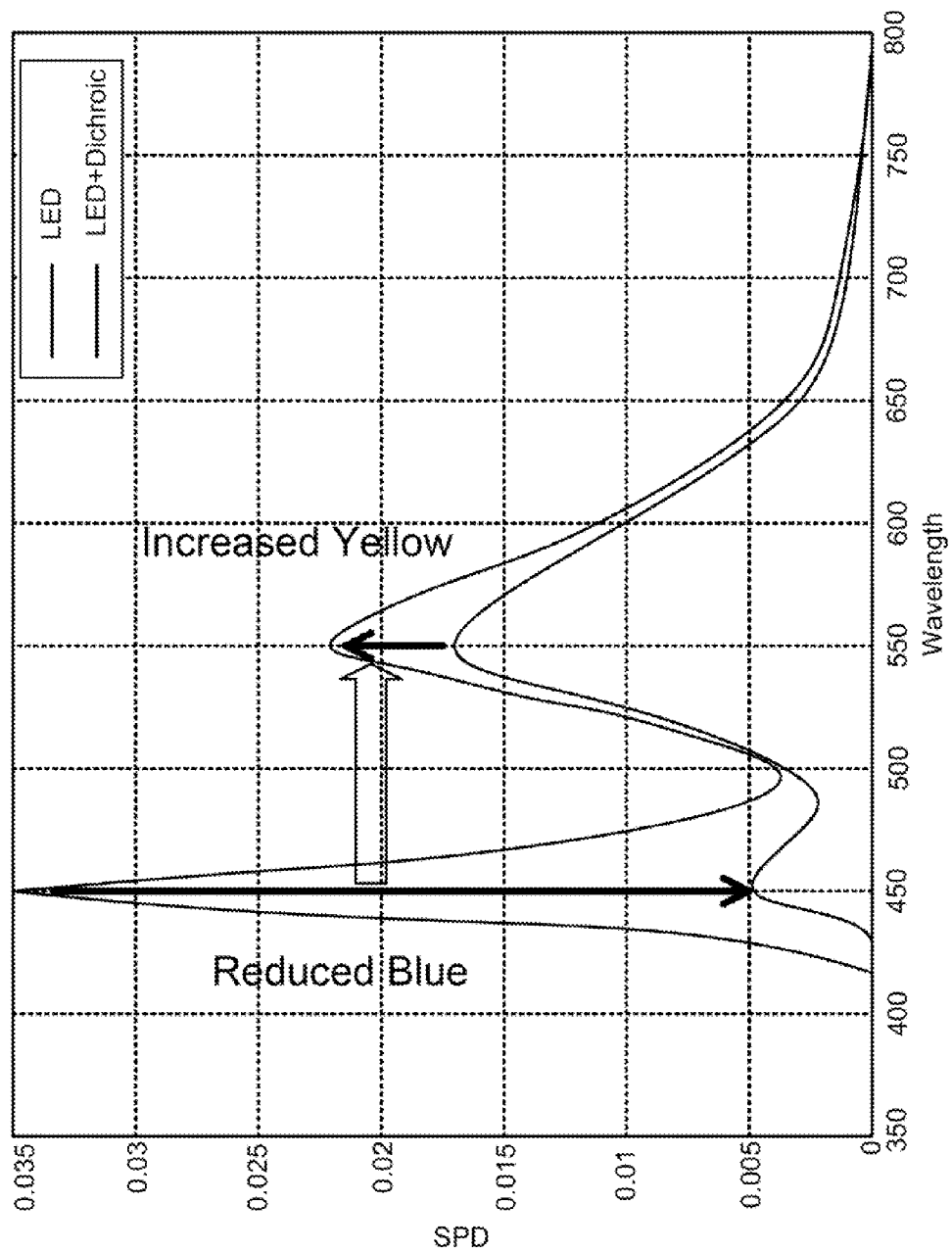
FIG. 7 illustrates the use of a dichroic filter.

Referring to FIG. 6, an exemplary spectral transmittance and reflectance of a dichroic filter is illustrated. Other spectral transmittance and reflectances may likewise be used, as desired. Other types of filters may likewise be used. FIG. 7 illustrates the spectra response of the light output as a function of wavelength selectively using a dichroic filter.

It is to be understood that the modification of the light output as a result of selectively increasing or decreasing the blue light output, as a result of using a Stokes technique, may be likewise applicable to lighting sources apart from attempting to modify the circadian rhythm of the viewer. Preferably, the light steering is performed by a liquid crystal based lens.

Figure 8:
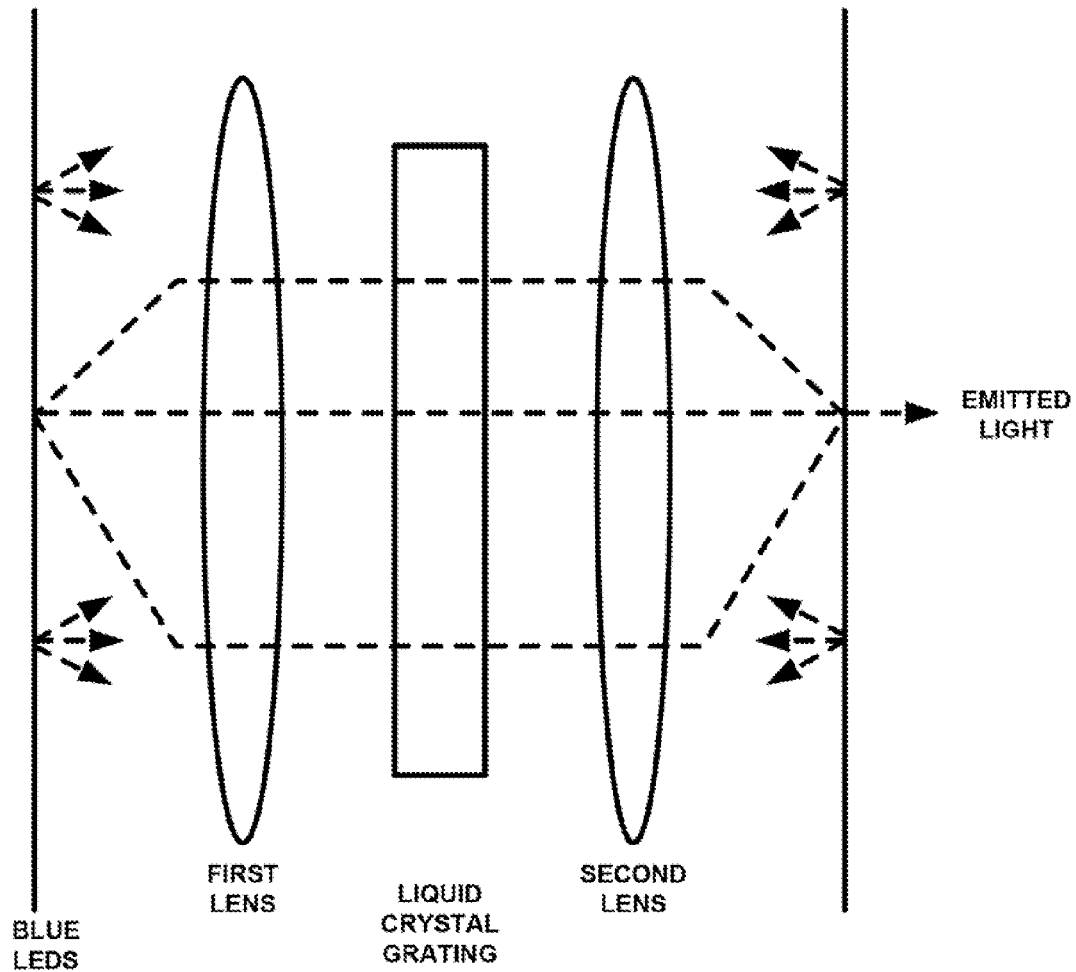
FIG. 8 illustrates beam steering using a liquid crystal lens.

For circadian modulation, it is preferable to have the spectra modulation be automatic and/or otherwise integrated with the light controller. While any suitable technique may be used to modify the spectrum, it is preferable that the technique involves few or no mechanically moving parts. Referring to FIG. 8, a liquid crystal layer may be used to achieve directional beam steering. In general, light from blue light emitting diodes (or otherwise a light source having a portion of its output that is generally blue) is collimated by a first lens, and then passes through the subsequent liquid crystal material. When a suitable signal is applied to the liquid crystal material, such as a periodic voltage waveform, it causes the liquid crystal material to change phase by $\pi$ (or other suitable amount). The liquid crystal material with a suitable signal applied thereto diffracts the incident light thereon by an angle. The first order diffraction is approximated by $\sin(\theta) = \lambda/d$, where d is the period of the liquid crystal grating. The diffraction angle ($\theta$) is determined by the radio of the wavelength ($\lambda$) and the period of the grating. After the light passes through the liquid crystal grating, the light is focused by the second lens onto an image plane, where a phosphor pattern may convert the blue light into yellow light and/or red light. The phosphor layer (or other material and/or structure) may covert the incident light to any other suitable one or more colors. When no signal is applied to the liquid crystal material, the blue light will be focused at different positions on the image plane. In this manner, the liquid crystal grating material may be used to modify the position of the light from the respective blue light emitting diodes on the image plane.

Figure 9:
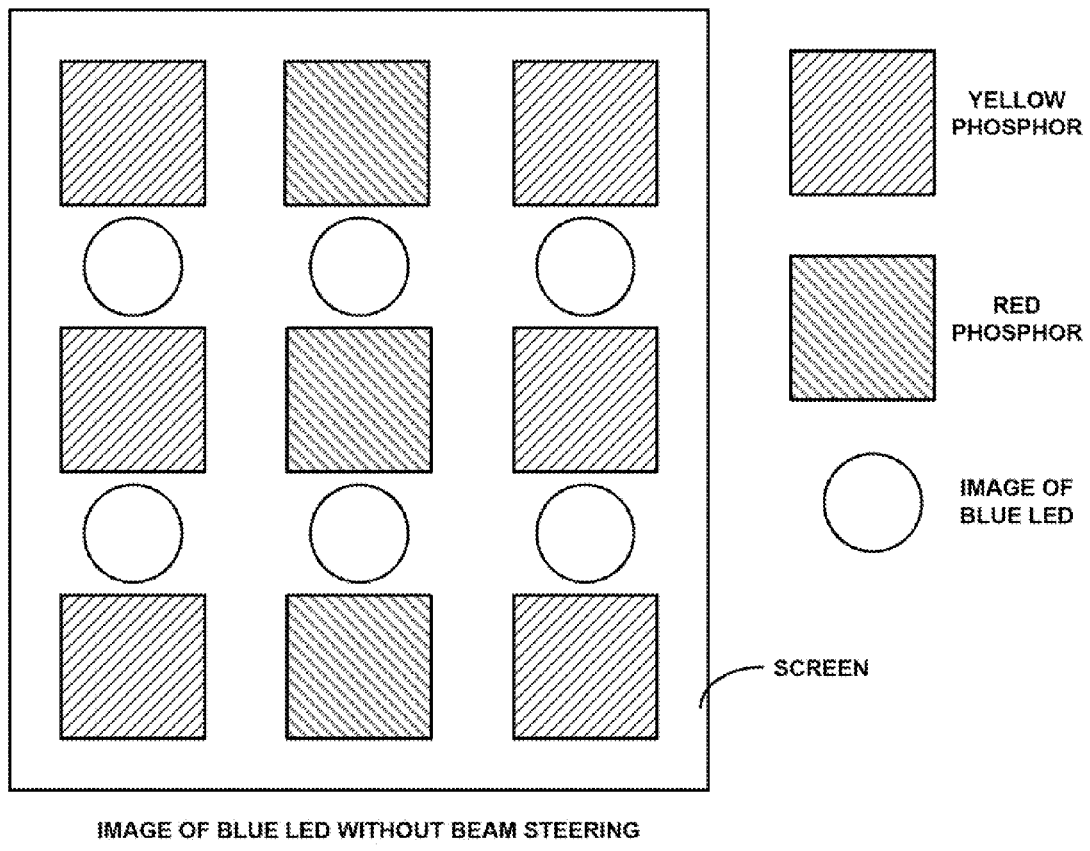
FIG. 9 illustrates a blue LED image without beam steering.

Referring to FIG. 9, an exemplary illustration is shown of the image plane without steering the light with the liquid crystal grating. It is noted that the image from the blue light emitting diodes are substantially incident on the regions of the image plane between the regions of the yellow phosphor and the red phosphor. In this manner, the blue light substantially emits from the device without substantially impacting any phosphor, thus the emitted light is primarily blue light.

Figure 10:
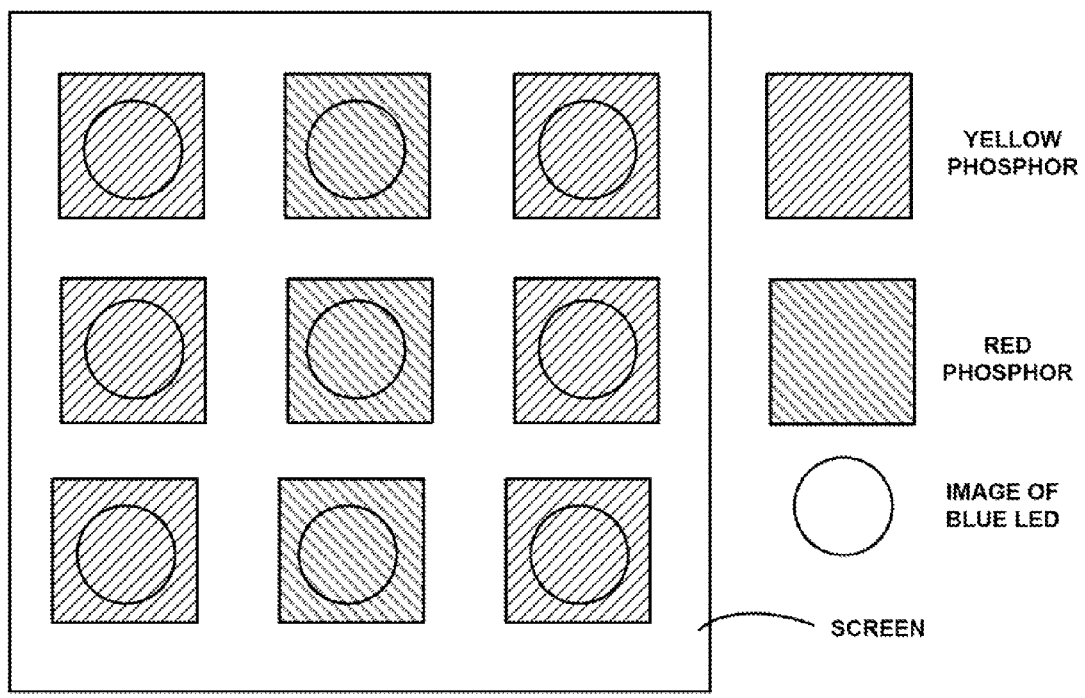
FIG. 10 illustrates a blue LED image with beam steering.

Referring to FIG. 10, if a voltage is applied to the liquid crystal grating, the liquid crystal grating bends the blue light, thus the image of the blue light from the light emitting diode tends to be shifted upward for the (+1) order of diffraction and shifts downward for the (−1) order of diffraction (not shown). The diffracted blue light substantially impacts the phosphors to an extent greater than without the voltage being applied, in such a manner that converts blue light into yellow light and/or red light depending on the arrangement of the phosphors.

In other embodiments, the system may overlap the blue light emitting diode image with the phosphor when the liquid crystal does not have an applied voltage and steer away from the phosphor when the liquid crystal has an applied voltage. In other embodiments, the system may select among a plurality of different applied voltage levels, including multiple applied non-zero voltages to diffract the light a suitable amount. Other embodiments may include a different amount of yellow and/or red phosphors so that the resulting color may be adjusted. Other embodiments may include one or more different phosphors, so that further color enhancement may be achieved. In other embodiments, the blue light may substantially impact the phosphors without an applied voltage and may substantially not impact the phosphors with the applied voltage.

In other embodiments, the amount of steering may be modified so that a plurality of different color outputs may be achieved. For example, at a first amount of steering (such as no steering) the output may be substantially blue since a minimal amount of phosphor is impacted. At a second amount of steering, a first set of phosphors may be selected to provide a selected output. By way of example, the second amount of steering may be primarily yellow with a limited amount of red light. At a third amount of steering, a third set of phosphors may be selected to provide a different selected output. By way of example, the third amount of steering may be primarily red with a limited amount of yellow light.

Figure 11:
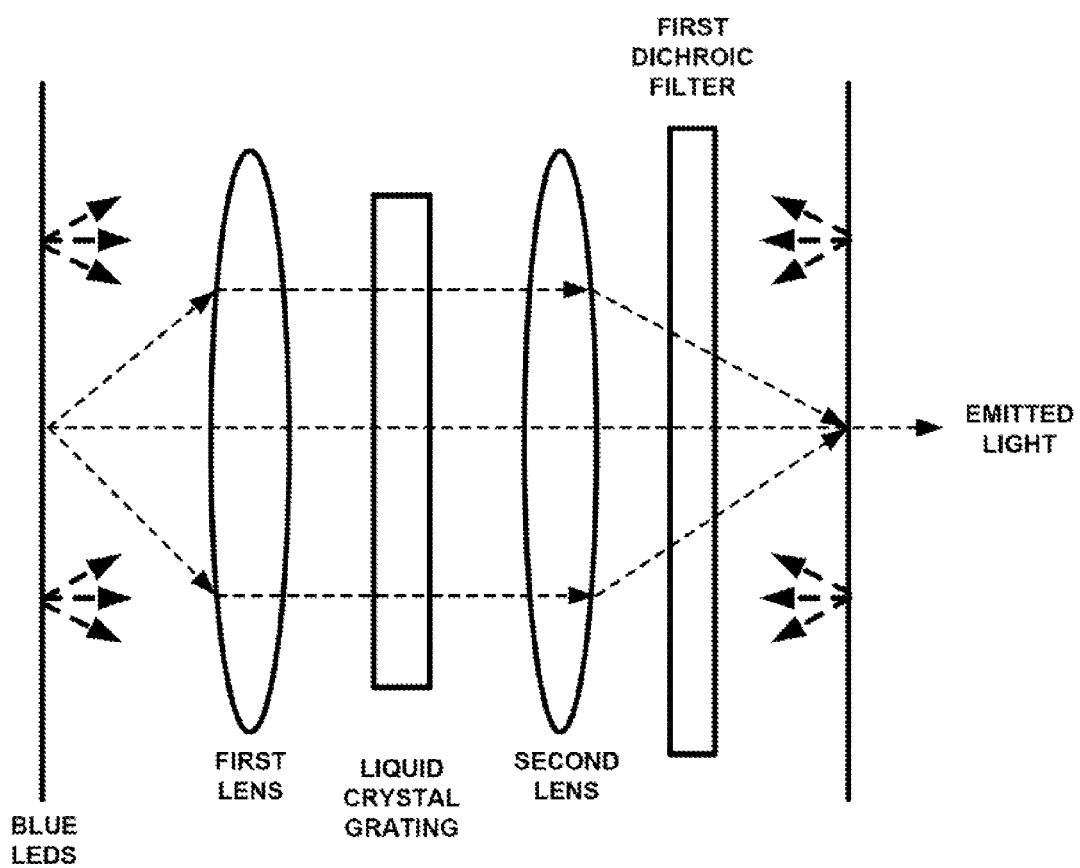
FIG. 11 illustrates a beam steering with a dichroic filter.

Referring to FIG. 11, the phosphor materials tends to result in emitted light in all directions, with some of the emitted light being directed back toward the combination of the second lens, the liquid crystal material, the first lens, and the light emitting diodes, and accordingly much of the light directed toward the liquid crystal layer tends to be significantly absorbed. The absorption of the light reduces the brightness of the device. To increase the efficiency of the device, a first dichroic filter may be included between the second lens and the phosphor material. The first dichroic filter is preferably designed to pass the blue light from the light source (and thus the liquid crystal grating layer), and otherwise reflect a substantial portion of the light from the phosphor material. For example, the filter may be a blue/yellow dichroic filter. In the case of a blue/yellow dichroic filter, the yellow light from the phosphor layer is reflected and thus tends to pass out the device, which increases the brightness of the yellow light. Other filters may be used.

Figure 12:
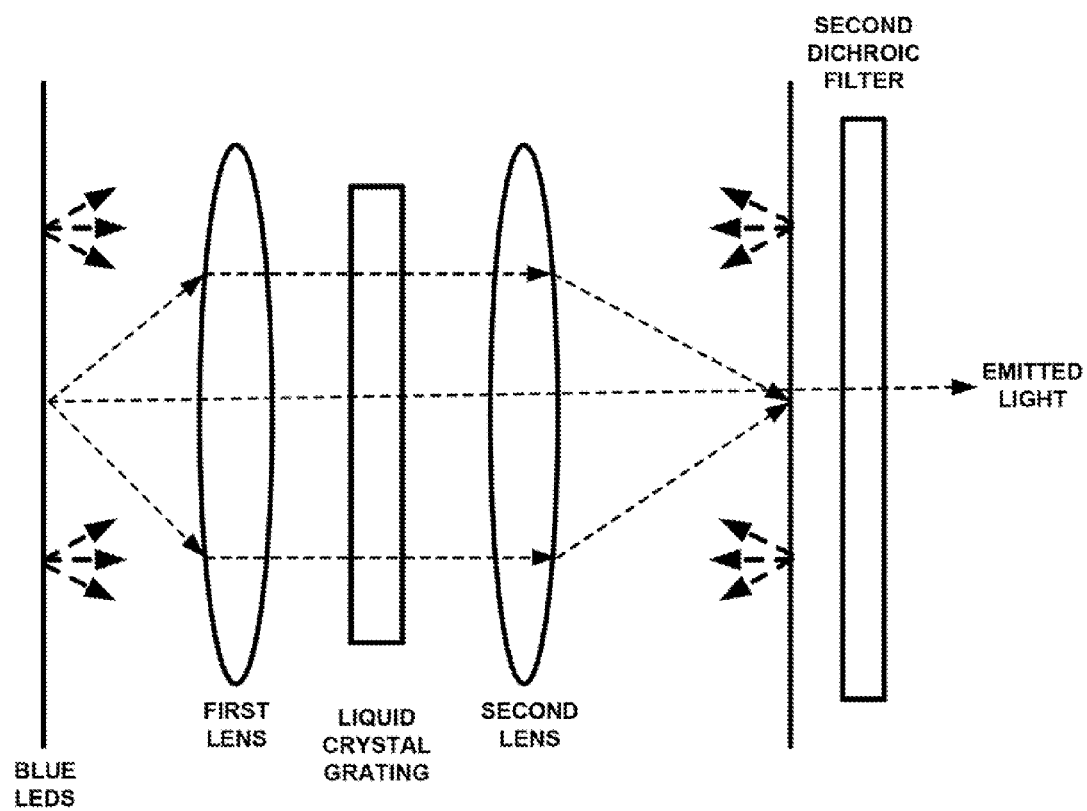
FIG. 12 illustrates a another beam steering with a dichroic filter.

Referring to FIG. 12, some of the light which should be converted to yellow light (or other light) by the phosphor material is not suitably converted and is therefore emitted as blue light. To increase the amount of effective light conversion, a second dichroic filter may be included after the phosphor material to selectively reflect back blue light so that is may be converted to a different spectrum by the phosphor material (such as yellow). The reflected blue light that is converted to a different spectrum is again emitted from the device. The dichroic filter is preferably patterned so that those regions that are intended to emit blue light pass through the second dichroic filter, and those regions that are intended to reflect blue light are co-located with the corresponding phosphor material. For example, the filter may be a yellow/blue dichroic filter. Other filters may be used.

Figure 13:
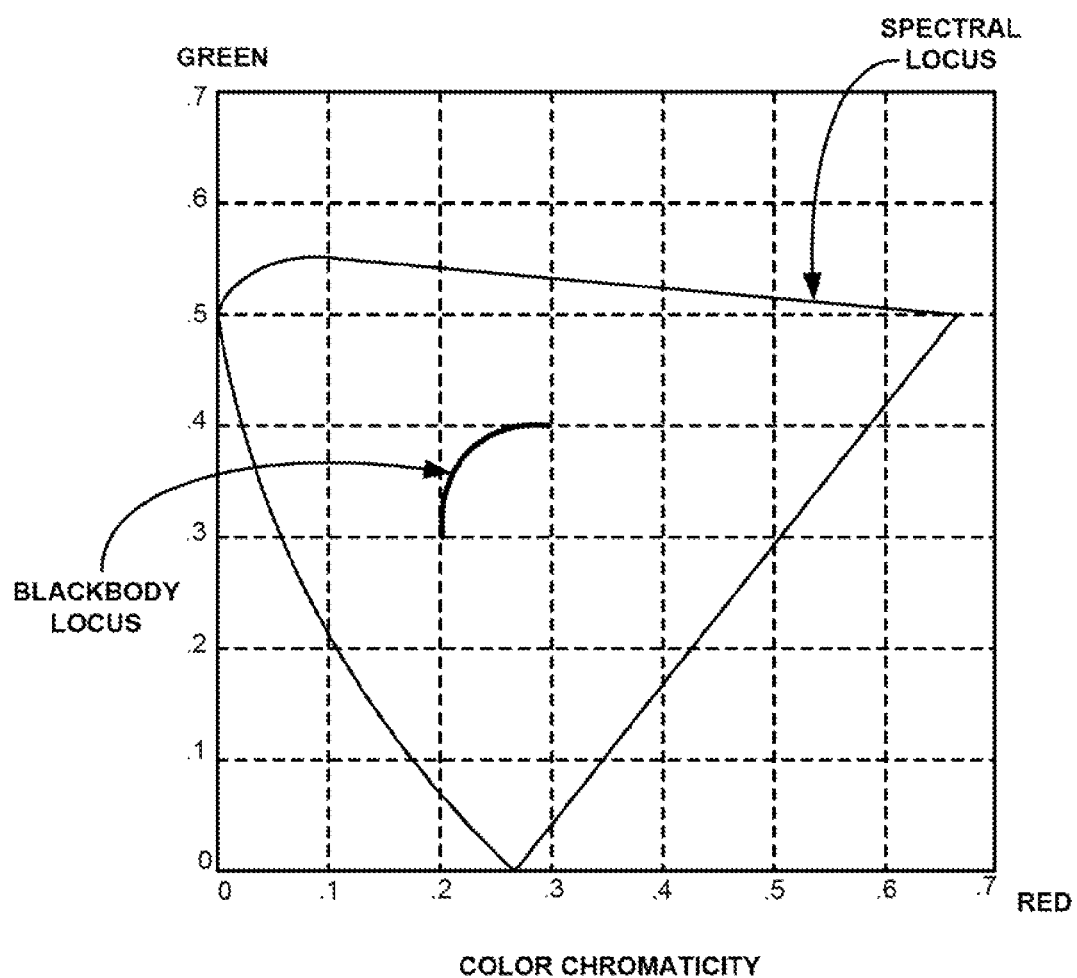
FIG. 13 illustrates a chromaticity diagram.
Figure 14:
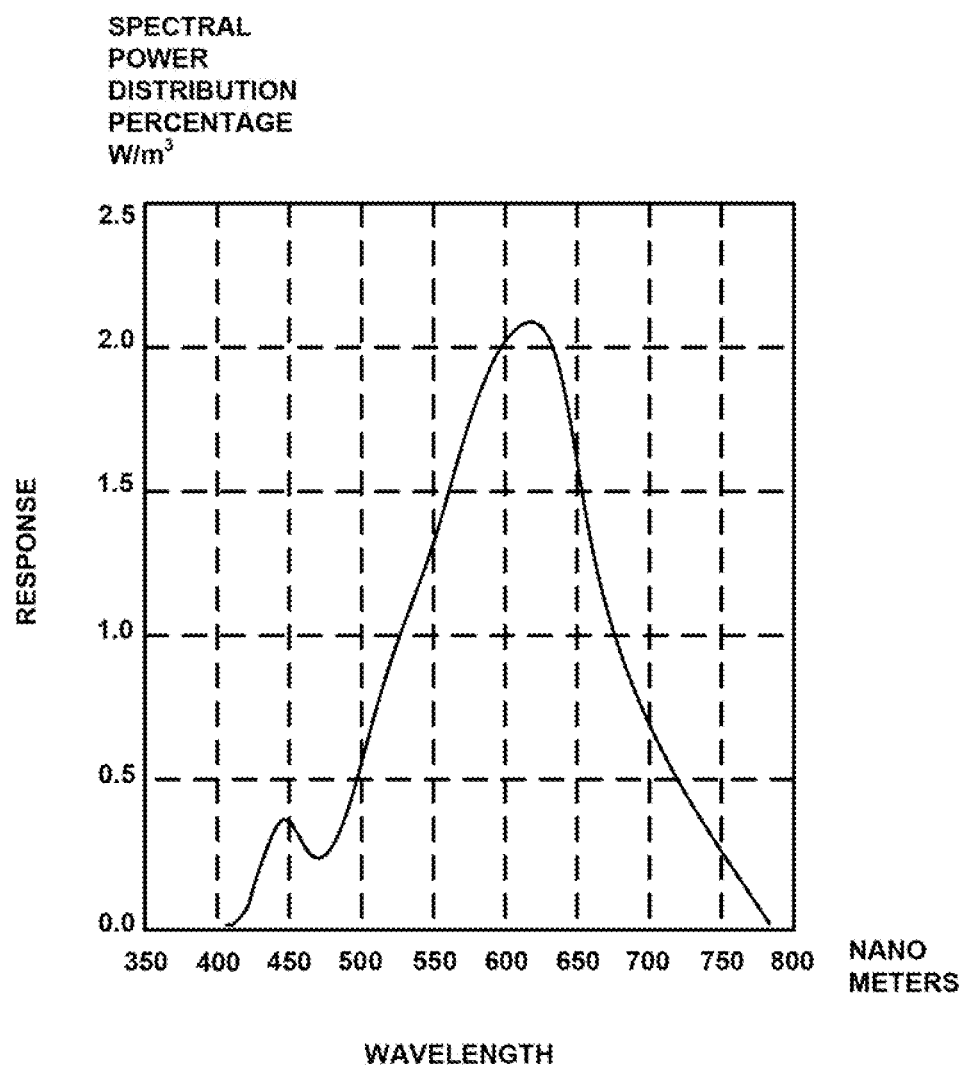
FIG. 14 illustrates a spectral response diagram.

In another embodiment, it is desirable to steer the light to achieve different correlated color temperatures (CCT), preferably with its white point chromaticity on the blackbody locus located as illustrated in FIG. 13. Referring also to FIG. 14, an exemplary spectra of a light emitting diode is shown, while FIG. 13 illustrates the chromaticity. The chromaticity of a light source may be on the blackbody locus to achieve true white illumination. Since the blackbody locus is a curve from lower CCT to higher CCT, at least three color mixtures may be used to achieve such white illumination.

Figure 15:
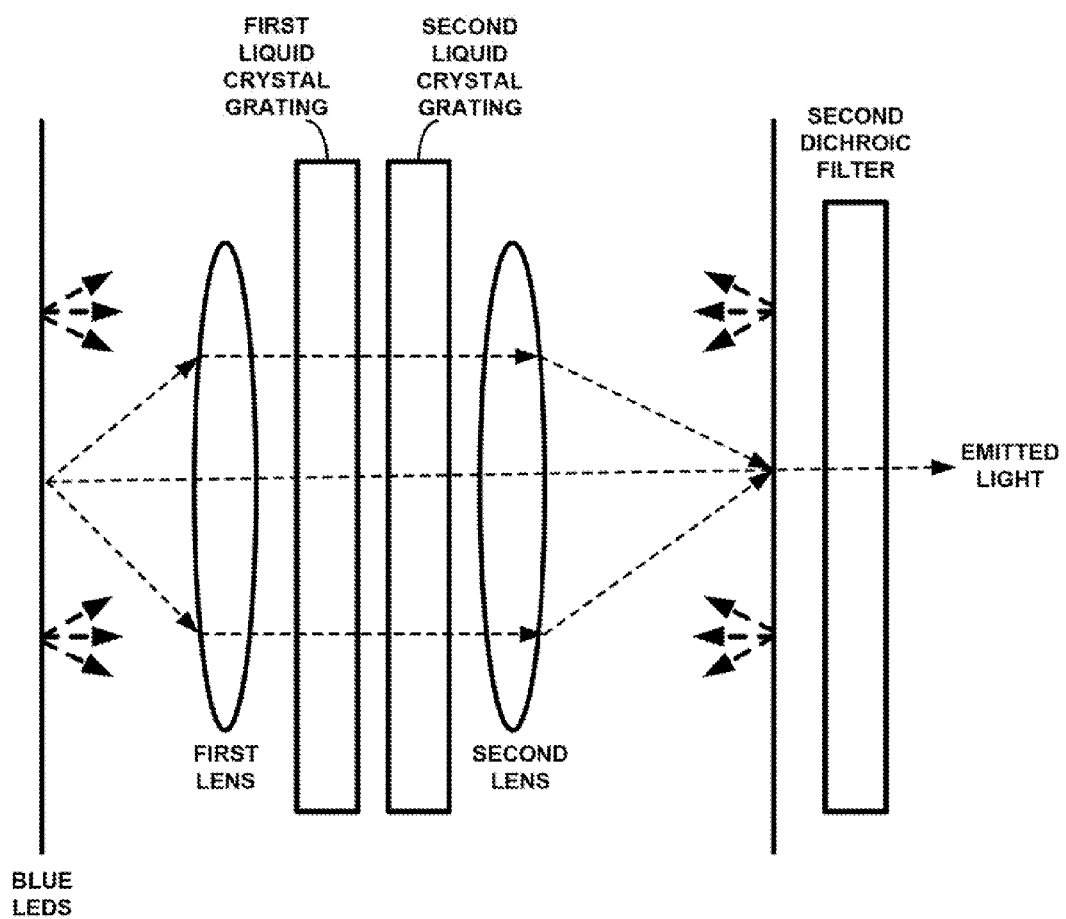
FIG. 15 illustrates color tuning with two liquid crystal gratings.

Referring to FIG. 15, one technique to tune the color chromaticity of the device is to include two or more liquid crystal gratings. One of the liquid crystal gratings may be used to adjust the ratio of the blue to the yellow+red light. The other of the liquid crystal gratings may be used to adjust the ratio of the yellow to red light. For example, the first liquid crystal grating may steer blue light from the light emitting diode up and down to modulate the blue to yellow+red ratio. The second liquid crystal grating may steer light left and right to modulate the red to yellow ratio. The angle of the steering may be controlled by the period of the liquid crystal grating. Other structures may likewise be used to adjust the color chromaticity of the device.

Figure 16:
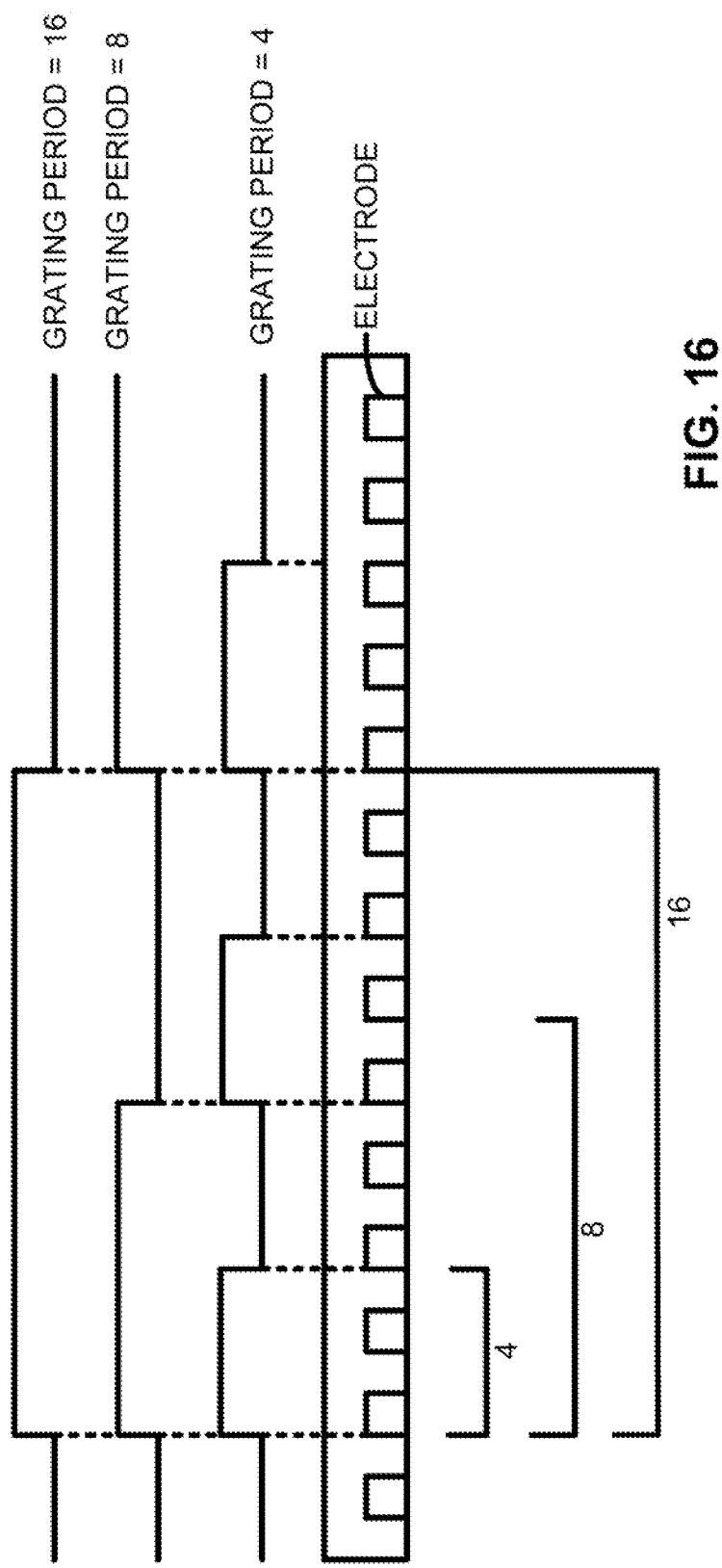
FIG. 16 illustrates an electrode configuration.

Referring to FIG. 16, an exemplary timing control technique is illustrated for selecting the grating periods. By selectively turning on and off the electrodes it may generate voltage waveforms having suitable periods.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A system for influencing a state of a user comprising:
   (a) a light source for emitting light having a spectral characteristic for influencing the state of the user;
   (b) a light controller selectively modifying the emitted light from said light source to modify said spectral characteristics of said emitted light;
   (c) an analysis engine that provides a signal to said light controller indicating a desired emission of said light, wherein said system uses an LCD layer to steer an amount of blue light of said spectral characteristics emitted from said light source, through said LCD layer and onto a material positioned on the opposite side of said LCD layer relative to said light source, and in a selectively time-varying spatial pattern projected on a surface of said material, said material capable of selectively converting the blue light into a different color, selection based on said time-varying pattern so as to result in said modified spectral characteristics.

2. The system of claim 1 wherein said system includes a liquid crystal layer that said selectively controls said emission of said light being in an optical path of said light.

3. The system of claim 2 wherein said system includes a first lens in said optical path of said light and that collimates said light, including said blue light.

4. The system of claim 3 wherein said system includes a second lens in said optical path of said light and that focuses said light on an image plane.

5. The system of claim 4 wherein said blue light is directed onto said material after passing through said liquid crystal layer, said first lens, and said second lens.

6. The system of claim 2 wherein said selectively directs is based upon a signal being applied to said liquid crystal layer.

7. The system of claim 1 wherein said material is a phosphor material.

8. The system of claim 7 wherein said phosphor material includes yellow phosphor.

9. The system of claim 8 wherein said phosphor material includes red phosphor.

10. The system of claim 7 wherein said phosphor material is patterned.

11. The system of claim 5 wherein said system further includes a first filter between said second lens and said material.

12. The system of claim 11 wherein said first filter is a dichroic filter.

13. The system of claim 11 wherein said first filter substantially passes blue light and substantially reflects light of a different color.

14. The system of claim 13 wherein said different color is yellow.

15. The system of claim 13 wherein said system further includes a second filter at a location on the opposing side of said material than said first filter.

16. The system of claim 15 wherein said second filter is spatially patterned.

17. The system of claim 15 wherein said second filter selectively reflects blue light.

18. The system of claim 17 wherein said second filter is a dichroic filter.

19. The system of claim 1 wherein said system includes at least two liquid crystal layers being in an optical path of said light to selectively adjust color chromaticity.

20. The system of claim 1 wherein said system selectively adjust color chromaticity.

* * * * *